United States Patent

Pomeroy et al.

[11] 4,448,313
[45] May 15, 1984

[54] SUPPORTING DEVICE

[76] Inventors: Glenn A. Pomeroy, #1 Revere La.; Carol L. Scrivens, 321 S. Logan St., both of Elyria, Ohio 44035

[21] Appl. No.: 399,728

[22] Filed: Jul. 19, 1982

[51] Int. Cl.³ .............................................. A47G 29/00
[52] U.S. Cl. ...................................... 211/71; 248/230; 248/231
[58] Field of Search ........................... 211/71, 86, 107; 248/231, 229, 311.2, 312.1, 313, 230; 24/252 R, 253

[56] References Cited

U.S. PATENT DOCUMENTS

| | | | |
|---|---|---|---|
| 587,912 | 8/1897 | Atwood | 248/230 |
| 646,969 | 4/1900 | Folger | 248/313 X |
| 691,364 | 1/1902 | Denckla | |
| 1,167,934 | 1/1916 | Roth | 211/71 X |
| 1,409,255 | 3/1922 | Smith | 211/71 |
| 1,669,747 | 5/1928 | Gerard | 248/229 |
| 1,799,079 | 3/1931 | Bemis | 248/312.1 |
| 2,689,995 | 9/1954 | Smith | 248/230 X |
| 2,918,202 | 12/1959 | Constantine et al. | 248/231 X |
| 3,612,460 | 10/1971 | Smith | 248/231 X |

FOREIGN PATENT DOCUMENTS 948459  1/1949  France ................................. 24/508

Primary Examiner—Ramon S. Britts
Assistant Examiner—Sarah A. Lechok

[57] ABSTRACT

This invention is directed to a new and novel method of supporting bed pans in a hospital atmosphere when not in use, thereby keeping them in a sterile condition until used. The supporting device contemplated by this invention consists of a pair of spring loaded clamps which are mounted on some support means. When mounted, bed pans are then inserted between the jaws of the spring loaded clamps and stored there until their use.

1 Claim, 4 Drawing Figures

SUPPORTING DEVICE

BACKGROUND OF THE INVENTION

Field of the Invention

The invention contemplated here is for use primarily in hospitals, but has numerous other uses, depending on the desire of the user. Patients who undergo surgery are constantly monitored subsequent to the surgery inorder to determine the progress of the patient and inorder to insure his return to normalcy. Quite often, the medical personnel must monitor the patients body waste for chemical composition and for quantity. It is necessary that the body waste be deposited in a sterile atmosphere in order to prevent the contamination of the specimen. The container in which the specimen is deposited is known as a bed pan and usually referred to by hospital personnel as a "hat". Prior to the applicants invention, it has been the general practise of many hospitals to set the bed pans on the floor of the room, or in some cases, on the floor of the bathroom. In any event, this places the bed pan in an atmosphere which is very conducive to contamination.

The applicant's invention drastically reduces the chance of contaminating the bed pans. The invention consists of a pair of spring loaded clamps mounted in unison on a permanent structure such as stand pipe coming off of a commode. The pair of clamps may thus be mounted at whatever height is desired. In this manner two bed pans may be supported at an elevated position by the clamps, thus removing them from the possibility of receiving foreign contamination. Another benefit derived from the applicant's invention is that it also insures that the bed pans do not get in the way of the patients and the janitorial people.

BRIEF DESCRIPTION OF THE INVENTED

The invention is directed to a device which is permanently mounted or a supporting structure at some elevated position. The invention consists of a plurality of clamps mounted on a supporting structure and designed for receiving and retaining bed pans in a hospital room situation thereby removing the bed pans from a situation where they could be contaminated.

DESCRIPTION OF THE PREFERRED EMBODIMENT

Figure 2:
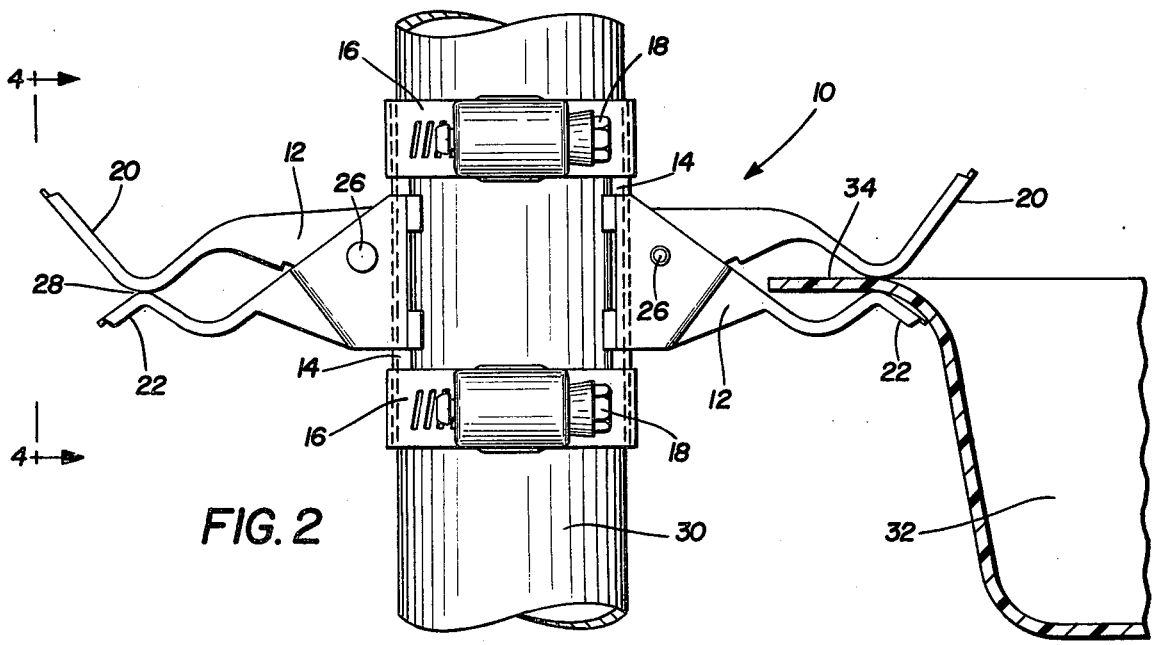
FIG. 2 is a side elevation view of the invention.

Referring to FIG. 2, the supporting device comprising the invention is shown generally at 10. A pair of spring loaded clamps 12 is integrally mounted on a support strap 14. The support strap 14 is in turn integrally connected to a pair of adjustable circular clamps 16. The clamps 16 are provided with adjusting bolts 18 enabling the supporting device 10 to be mounted on structures of various diameters and configurations.

Figure 1:
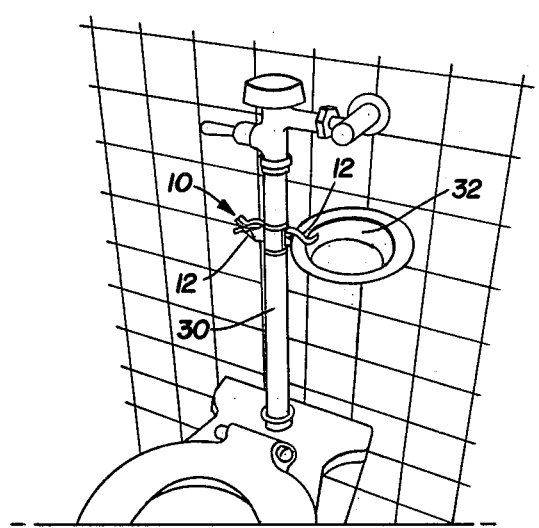
FIG. 1 is a plan view of the invention supporting one pan.
Figure 4:
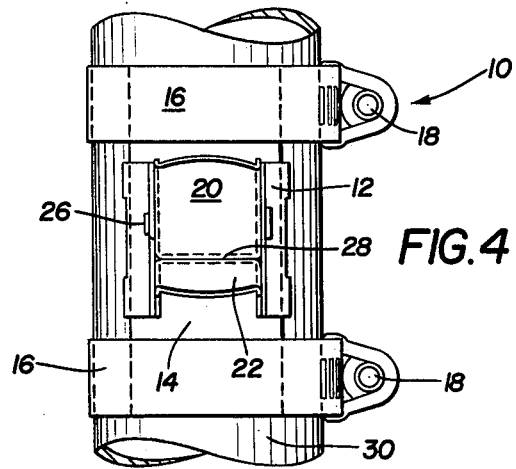
FIG. 4 is an end view of the invention taken along lines 4—4 of FIG. 2.
Figure 3:
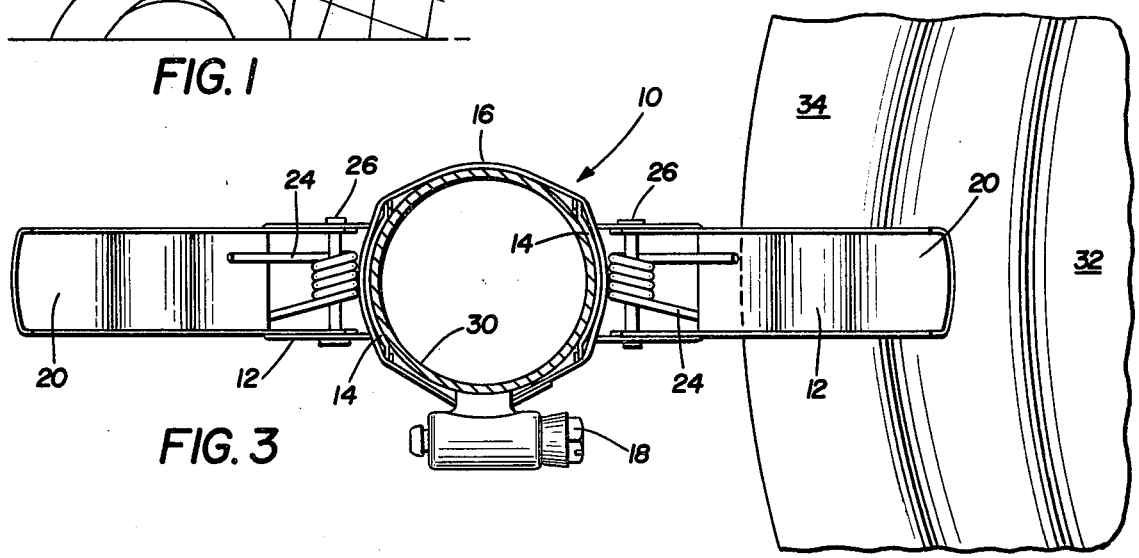
FIG. 3 is a top elevation view of the invention.

Referring to FIG. 3, it can be seen that the clamps 12 are in diametric opposition to each other, however, the invention could be used with the clamps 12 and support straps 14 mounted in other configurations. The clamps 12 terminate at their ends with a pair of arcuately designed lips, a top lip 20 and a bottom lip 22. The upper lip 20 is attached to a spring 24 and to a pivot point 26 thus being movable about the pivot point 26. The spring 24 is designed such that the lip 20 is resiliently biased against lip 22 pressurized thus is in pressuried contact with one another at a point 28.

In operation, the supporting device 10 is mounted on some structure, in this constance, a stand pipe 30. A pan 32 having rim 34 is forced between the lips 20 and 22 and held in place between the lips 20 and 22 as a result of the pressured being exerted by the spring 24 onto the top lip 20. The lips 20 and 22 are designed at their ends such that they also serve as guides when the rim 34 is being inserted between the lips 20 and 22. In this manner, it is not necessary for the operator to touch the clamp 12. The surface at the point 28 is generally smooth and the terminating portion of the bottom lip 22 is arcuately designed such that it provides further support for the pan 32.

The supporting device 10 is preferably made out of stainless steel because of the anti-corrosion properties that stainless steel has. However, the invention may be made out of other material that have structural strength sufficient to support the hospital pans.

What is claimed is:

1. A supporting device, including:
   a pair of circular adjustable mounting clamps;
   a pair of support members integrally attached to said mounting clamps, said support members, each being perpendicular to said mounting clamps;
   a non-pivotal first lip member, rigidly affixed to each said support member, said first lip member being arcuate in configuration at one end and terminating in a triangular flare at the other end;
   a bearing member affixed to said first lip member at the end terminating in a generally triangular flare,
   a second lip member, pivotally attached to said first lip member by said bearing member such that said second lip member is superimposed on said first lip member and is rotatable about said bearing member, said second lip member being arcuate in configuration at one end thereof; and
   spring means attached to said bearing member for resiliently biasing said second member against said first lip member, said first and second lip member being in pressurized contact with one another at opposed points defined by said arcuate ends and being adapted for resiliently gripping a pan at the edge thereof, with said first lip member contacting one surface of said pan and said second lip member contacting another surface of said pan.

* * * * *